United States Patent
Ratton et al.

(10) Patent No.: US 12,258,312 B2
(45) Date of Patent: Mar. 25, 2025

(54) CARBONYL COMPOUNDS, METHODS FOR PREPARING SAME AND USES THEREOF

(71) Applicant: Global Bioenergies, Evry (FR)

(72) Inventors: Serge Ratton, Saint Germain en Laye (FR); Marc Lemaire, Villeurbanne (FR); Luc Mathis, Le Kremlin Bicetre (FR); Estelle Metay, Villeurbanne (FR)

(73) Assignee: Global Bioenergies, Evry (FR)

( * ) Notice: Subject to any disclaimer, the term of this patent is extended or adjusted under 35 U.S.C. 154(b) by 608 days.

(21) Appl. No.: 17/635,545

(22) PCT Filed: Aug. 17, 2020

(86) PCT No.: PCT/EP2020/072990
§ 371 (c)(1),
(2) Date: Feb. 15, 2022

(87) PCT Pub. No.: WO2021/032673
PCT Pub. Date: Feb. 25, 2021

(65) Prior Publication Data
US 2022/0340512 A1   Oct. 27, 2022

(30) Foreign Application Priority Data
Aug. 16, 2019   (FR) ........................ 1909244

(51) Int. Cl.
C07C 67/44   (2006.01)
C07C 45/50   (2006.01)
C07C 51/235   (2006.01)

(52) U.S. Cl.
CPC .............. *C07C 67/44* (2013.01); *C07C 45/50* (2013.01); *C07C 51/235* (2013.01)

(58) Field of Classification Search
CPC ................... C07C 67/44; C07C 45/50
See application file for complete search history.

(56) References Cited

U.S. PATENT DOCUMENTS

| | | | |
|---|---|---|---|
| 2011/0269996 A1* | 11/2011 | Teles | C07C 45/28 568/398.8 |
| 2019/0062242 A1 | 2/2019 | Chen et al. | |
| 2019/0100711 A1 | 4/2019 | Patil et al. | |

FOREIGN PATENT DOCUMENTS

| | | |
|---|---|---|
| EP | 1710225 A1 | 10/2006 |
| JP | 2014108944 A * | 6/2014 |
| WO | 2010033976 A2 | 3/2010 |
| WO | 2018119466 A1 | 6/2018 |
| WO | 2020176505 A1 | 9/2020 |

OTHER PUBLICATIONS

Wang, et al., Olefin oligomerization via new and efficient Bronsted acidic ionic liquid catalyst systems, Chinese Journal of Catalysis, vol. 39, No. 6, pp. 1110-1120 (Year: 2018).*
Pirozhkov, et al., Carbonylation of isobutylene, its oligomers, and n-olefins by carbo monoxide in the presence of boron fluoride complexes with propionic, acetic or monochloroacetic acids, Izvestiya Akademii Nauk SSSR, Seriya Khimicheskaya, (7), 1543-41, 1 page abstract (Year: 1976).*
Khodakov et al, "Oligomerization of Isobutylene on Oxides Communication 3. Catalytic Properties of Alumina-Rhenium Catalysts", Plenum Publishing Corporation, 1983, 99.1807-1809, vol. 32.
Liu et al., "Highly Efficient Trimerization of Isobutene Over Silica Supported Chloroaluminate Ionic Liquid Using C4 Feed", Catalysis Today, 2013, pp. 41-48, vol. 200.
Newman et al, "Steric Effect of Neopentyl Groups in the Reaction of Olefins with Peracids", Journal of the American Chemical Society, 1967, pp. 2059-2062, vol. 89, No. 9.
Wang et al, "Olefin Oligomerization via New and Efficient Bronsted Acidic Ionic Liquid Catalyst Systems", Chinese Journal of Catalysis, 2018, pp. 1110-1120, vol. 39, No. 6.

* cited by examiner

*Primary Examiner* — Yate' K Cutliff
(74) *Attorney, Agent, or Firm* — Thompson Coburn LLP; Steven M. Ritchey

(57) ABSTRACT

The present application relates to a compound of the following formula (I)

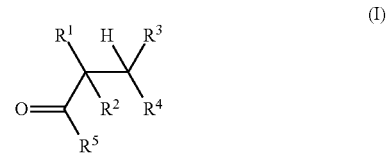

in which —$R^1$, $R^2$, $R^3$ and $R^4$ represent independently of each other H or a ($C_1$-$C_{30}$) alkyl group,
the total sum of the number of carbon atoms of $R^1$, $R^2$, $R^3$ and $R^4$ being equal to 6+4$x$, $x$ being a whole number of between 1 and 6,
provided that:
  at most two of the groups $R^1$, $R^2$, $R^3$ and $R^4$ are H,
  $R^5$ represents H, OR, or NR'R"
  R, R' and R", identical or different, represent H, a (C1-C10) alkyl group,
at least one of groups $R^1$, $R^2$, $R^3$ or $R^4$ comprises or is a tertiobutyl group. (I) the method for preparing same and the uses thereof as a plasticising lubricant, surfactant or in a cosmetic composition.

10 Claims, No Drawings

CARBONYL COMPOUNDS, METHODS FOR PREPARING SAME AND USES THEREOF

CROSS-REFERENCE TO RELATED APPLICATIONS

This application is a U.S. National Phase application of PCT/EP2020/072990 filed on Aug. 17, 2020, claiming the benefit of French Application No. 1909244, filed on Aug. 16, 2019, both of which are incorporated herein by reference in their entireties.

The subject of the present invention concerns novel isomers of branched carbonyl alkanes, alone or in mixtures, and methods for preparing the same. It also concerns the use of said compounds alone or in mixtures.

Functionalised branched alkanes comprising a high number of carbon atoms, in particular 8 or more carbon atoms, have varied applications. They can be particularly used as surfactants, emollients, solvents or monomers for the preparation of varied polymers.

However, these compounds are generally derived from fossil resources, chiefly petroleum. In addition to having a negative effect on the environment the use of fossil, and particularly petroleum resources, leads to alkanes having impurities of aromatic compound type. Additionally, to obtain higher alkanes particularly having a number of carbon atoms of at least 16, it is necessary to have recourse to oligomerization reactions, these reactions resulting in mixtures of olefins and then mixtures of alkanes (after hydrogenation of the olefins) having n carbon atoms comprising impurities in n−4 and n+4 carbon atoms when olefins are obtained via oligomerization. Said impurities are undesirable.

It is the object of the present invention to provide novel carbonyl compounds able to be given particular use as plasticizer, lubricant, surfactant or for cosmetic applications, said compounds being biosourced.

The present invention therefore concerns a compound of following formula (I):

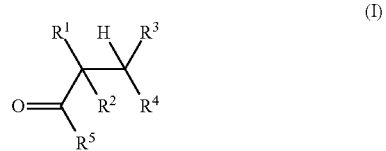

where:
$R^1$, $R^2$, $R^3$ and $R^4$ are each independently H or a ($C_1$-$C_{30}$) alkyl group, the total sum of the number of carbon atoms of $R^1$, $R^2$, $R^3$ et $R^4$ being equal to 6+4x, x being an integer of 1 to 6, provided that:
at most two among the groups $R^1$, $R^2$, $R^3$ and $R^4$ are H, when one of groups $R^1$ or $R^2$ is H or when groups $R^1$ and $R^2$ are H, then the groups $R^3$ and $R^4$ are ($C_1$-$C_{30}$) alkyl groups, and
when one of groups $R^3$ or $R^4$ is H or when groups $R^3$ and $R^4$ are H, then the groups $R^1$ and $R^2$ are ($C_1$-$C_{30}$) alkyl groups;
$R^5$ is H, OR, NR'R"
R, R' and R", the same or different, are H, a (C1-C10) alkyl group.

Preferably, the main chain comprises at least one tert-butyl group (at least one of groups $R^1$, $R^2$, $R^3$ or $R^4$ comprises or is a tert-butyl group), preferably the tert-butyl group is a terminal group.

Preferably, the total sum of the number of carbon atoms of $R^1$, $R^2$, $R^3$ and $R^4$ being equal to 6+4x, x is 1, 4 or 6 or x is 2, 3, 4, 5, 6 and $R^5$ is OR, NR'R".

Therefore, the present invention concerns a compound of following formula (I):

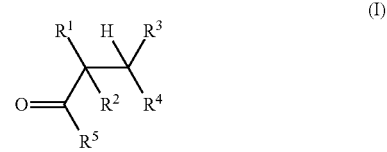

where:
$R^1$, $R^2$, $R^3$ and $R^4$ are each independently H or a ($C_1$-$C_{30}$) alkyl group, the total sum of the number of carbon atoms of $R^1$, $R^2$, $R^3$ and $R^4$ being equal to 6+4x, x being an integer of 1 to 6, provided that:
at most two among the groups $R^1$, $R^2$, $R^3$ and $R^4$ are H, $R^5$ is H, OR, NR'R"
R, R' and R", the same or different, are H, a ($C_1$-$C_{10}$) alkyl group, Preferably the main chain comprises at least one tert-butyl group (at least one of groups $R^1$, $R^2$, $R^3$ or $R^4$ comprises or is a tert-butyl group), preferably the tert-butyl group is a terminal group.

Preferably x is 1.

The formula (I) compounds correspond to isomers of branched carbonyl alkanes depending upon the type of above-mentioned $R^5$ group.

These compounds comprise overall (without counting group $R^5$) 8+4x carbon atoms, which corresponds to the total number of carbon atoms of the groups $R^1$, $R^2$, $R^3$ and $R^4$ and the two carbon atoms carrying these groups (the whole is considered hereafter to be a branched hydrocarbon chain having 8+4x carbon atoms). The formula (I) compounds of the invention are therefore branched compounds with a main chain comprising 12, 16, 20, 24, 28 or 32 carbon atoms and carrying a side chain $COR^5$ such as defined above. Preferably, the number of carbon atoms is 8+4x, x is 1, 4 or 6 or x is 2, 3, 4, 5, 6 and $R^5$ is OR, NR'R".

Preferably, the main chain comprises at least one tert-butyl group (at least one of groups $R^1$, $R^2$, $R^3$ or $R^4$ comprises a tert-butyl group or is a tert-butyl group), preferably the tert-butyl group is a terminal group.

In above-mentioned formula (I), according to one embodiment, one of groups $R^1$, $R^2$, $R^3$ or $R^4$ comprises a tert-butyl group. In one embodiment, in formula (I), one of groups $R^1$, $R^2$, $R^3$ or $R^4$ is a tert-butyl group.

In one embodiment, in formula (I), one of groups $R^1$, $R^2$, $R^3$ or $R^4$ comprises a tert-butyl group and meets the formula -A-C($CH_3$)$_3$, A being an alkylene radical having 1 to 6 carbon atoms.

The term "alkylene" according to the invention designates a radical having 1 to 6 carbon atoms, and preferably 1 to 4 carbon atoms. An alkylene radical corresponds to an alkyl radical such as defined herein from which one hydrogen atom has been removed.

In the present invention, by $C_t$-$C_z$ it is meant a carbon chain possibly having t to z carbon atoms, for example $C_1$-$C_3$ is a carbon chain possibly having 1 to 3 carbon atoms.

In the invention, an alkyl group designates a linear or branched, saturated, aliphatic hydrocarbon group having 1 to 30 carbon atoms unless otherwise stated. As examples, mention can be made of methyl, ethyl, n-propyl, isopropyl, butyl, isobutyl, tertbutyl or pentyl groups, or also undecenyl, lauryl, palmyl, oleyl, linoleyl, erucyl, terpenyl and ricinoleyl groups.

The present invention also concerns a mixture of isomers of branched carbonyl alkanes, each branched carbonyl alkane comprising a branched hydrocarbon chain and a side chain of formula $COR^5$, $R^5$ being such as defined above, said branched hydrocarbon chain of each branched carbonyl alkane having 8+4x carbon atoms, x being an integer of 1 to 6. Preferably, the number of carbon atoms is 8+4x, x being 1, 4 or 6 or x is 2, 3, 4, 5, 6 and R5 is OR, NR'R".

Preferably, the main chain comprises at least one tert-butyl group (at least one of groups R1, R2, R3 or R4 comprises a tert-butyl group or is a tert-butyl group), preferably the tert-butyl group is a terminal group.

In one embodiment, the mixture of isomers of branched carbonyl alkanes of the invention comprises at least two compounds of formula (I) such as defined above.

In one embodiment, the mixture of isomers of branched carbonyl alkanes of the invention comprises at least two compounds of formula (I) such as defined above.

In one embodiment, the mixtures of the invention are such that all the compounds of formula (I) such as defined above comprise a branched hydrocarbon chain having 8+4x carbon atoms, x being such as defined above and being the same for all the compounds of said mixture and comprising a side chain of formula $COR^5$.

The present invention also concerns a method for preparing a compound such as defined above, in particular meeting formula (I), or the mixture such as defined above comprising a carbonylation step in particular hydro-, hydroxy-, alkoxy-, amido-carbonylation, of at least one isomer of branched olefins or mixture of isomers of branched olefins, each branched olefin being formed of a hydrocarbon chain having 8+4x carbon atoms, x being such as defined above.

The carbonylation step corresponds to a step to add a CO compound to which the addition has been made of H2 for hydrocarbonylation, of $H_2O$ for hydroxycarbonylation, of $R^5$—OH for alkoxycarbonylation and of R'R"—NH for amidocarbonylation.

Preferably, the carbonylation step is performed via organometallic catalysis, in particular using a Rh or Co catalyst for example.

The carbonylation step is conducted at a temperature of between 40° C. and 150° C., preferably between 70° C. and 120° C.

In one embodiment of the method of the invention, the isomers or branched olefins are of following formula (II):

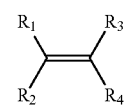

where $R^1$, $R^2$, $R^3$ and $R^4$ are such as defined in formula (I).
As mentioned above, in formula (II):
at most two among the groups $R^1$, $R^2$, $R^3$ and $R^4$ are H, when one of groups $R^1$ or $R^2$ is H or when groups $R^1$ and $R^2$ are H, then the groups $R^3$ and $R^4$ are ($C_1$-$C_{30}$) alkyl groups, and
when one of groups $R^3$ and $R^4$ is H, or when groups $R^3$ and $R^4$ are H, then the groups $R^1$ and $R^2$ are ($C_1$-$C_{30}$) alkyl groups.

Preferably, the main chain comprises at least one tert-butyl group (at least one of groups $R^1$, $R^2$, $R^3$ or $R^4$ comprises or is a tert-butyl group), preferably the tert-butyl group is a terminal group.

In one embodiment of the method of the invention, the isomers of branched olefins are of following formula (II):

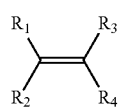

where $R^1$, $R^2$, $R^3$ and $R^4$ are such as defined above in formula (I).

As mentioned above, in formula (II):
at most two among the groups $R^1$, $R^2$, $R^3$ and $R^4$ are H, $R^1$, $R^2$, $R^3$ or $R^4$ comprises or is a tert-butyl group, preferably the tert-butyl group is a terminal group.

The method of the invention can use a branched olefin of formula (II) or a mixture of branched olefins of formula (II) comprising the same number of carbon atoms, or a different number of carbon atoms, preferably the same number of carbon atoms.

In one embodiment of the method of the invention, the mixture of isomers of branched olefins comprises at least two isomers of branched olefins of formula (II).

The olefins of formula (II) therefore meet one of the following formulas:

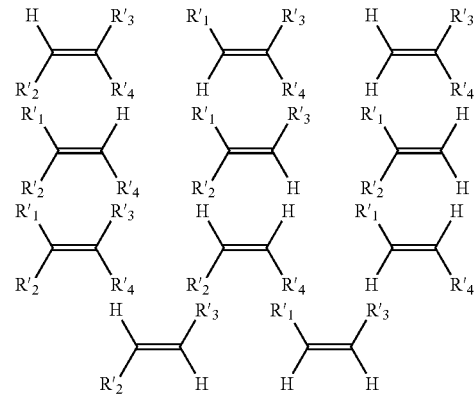

where $R'_1$, $R'_2$, $R'_3$ and $R'_4$ are ($C_1$-$C_{30}$) alkyl groups. preferably:

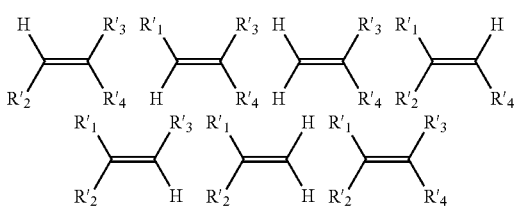

In one embodiment, the olefins of formula (II) may comprise two hydrogen atoms, one corresponding to the group $R'_1$ or $R'_2$ and the other to the group $R'_3$ or $R'_4$.

As mentioned above, the formula (II) compounds are branched compounds having a total of 8+4x carbon atoms with x between 1 and 6. The formula (II) compounds are therefore branched compounds with a main chain comprising 12, 16, 20, 24, 28 or 32 carbon atoms. Preferably the number of carbon atoms is equal to 8+4x, x is 1, 4 or 6 or x is 2, 3, 4, 5, 6 and $R^5$ is OR, NR'R".

The mixture of isomers of branched olefins of the invention is a mixture comprising at least two olefins of formula (II). Preferably, the mixtures of the invention are such that all the formula (II) compounds such as defined above have 8+4x carbon atoms, x being such as defined above and being the same for all the compounds of said mixture. Preferably, the number of carbon atoms is equal to 8+4x, x is 1, 4 or 6, or x is 2, 3, 4, 5, 6 and $R^5$ is OR, NR'R".

The branched olefins or mixture of isomers of branched olefins of the invention, in particular when n is 16, 24 or 32, can be obtained by dimerizing a mixture of isomers of branched olefins having n/2 carbon atoms.

Therefore, the branched olefins or mixture of isomers of branched olefins such as defined above are obtained by dimerizing a mixture of isomers of branched olefins having 4+2x carbon atoms with x being an even number defined above, preferably obtained from bioresources.

Therefore, the branched olefins having 16 carbon atoms can be obtained by dimerizing branched olefins having 8 carbon atoms. The branched olefins having 24 carbon atoms can be obtained by dimerizing branched olefins having 12 carbon atoms. The branched olefins having 32 carbon atoms can be obtained by dimerizing branched olefins having 16 carbon atoms.

The dimerization step can be performed in the presence of a catalyst selected from among Brønsted acids in solution, e.g. $H_2SO_4$, $H_3PO_4$, HF; solid Brønsted acids e.g. organic resins, clays zeolites, silica supported $H_3PO_4$; Lewis acids e.g. $ZnCl_2$, $AlCl_3$; organometallic compounds e.g. Ni complexes, mixtures of Ni complexes and Al; ionic liquids e.g. [BMIm][N($CF_3SO_2$)$_2$]/HN($CF_3SO_2$)$_2$; clays with lamellar structure such as Montmorillonite; organic resins such as Amberlysts, sulfonic resin; organometallic compounds such as [LNiCH$_2$R$^9$][AlCl$_4$] where L=PR$^{10}$, R$^9$ is a linear or branched alkyl having 9 carbon atoms and R$^{10}$ is a —CH$_2$—R$^9$ group.

The dimerization step is preferably conducted at a temperature of between 30 and 250° C.

In particularly advantageous manner, the branched olefins having 8 and 12 carbon atoms are obtained from isobutene. Preferably, said isobutene is obtained from bioresources in particular such as described in applications WO2012052427, WO2017085167 and WO2018206262, for example from polysaccharides (sugars, starches, celluloses, etc).

In particularly advantageous manner, the obtaining of branched olefins by dimerization allows branched olefins or a mixture of branched olefins to be obtained free of n–4 and n+4 olefins.

The branched olefins or mixture of isomers of branched olefins of the invention can also be obtained by co-dimerization of at least two mixtures of branched olefins respectively having m and p carbon atoms so that m+p=n.

Preferably, at least one of the starting olefins (olefin comprising m or p carbon atoms) comprises at least one tert-butyl group (C(CH$_3$)$_3$), preferably comprises a tert-butyl group at terminal position.

The co-dimerization step can also be followed by one or more purification steps, for example by distillation, for example to remove the n–4 and n+4 olefins.

The branched olefins or mixture of isomers of branched olefins of the invention can also be obtained by metathesis of at least two mixtures of branched olefins respectively having m and p carbon atoms so that m+p is higher than n. The metathesis step can also be followed by one or more purification steps, for example by distillation, for example to remove the n–4 and n+4 olefins.

Preferably, the branched olefins having m+p carbon atoms are obtained from bioresources and in particular from isobutene obtained with the method described in applications WO2012052427, WO2017085167 and WO2018206262, for example from polysaccharides (sugars, starches, celluloses, etc).

Regarding methods using co-dimerization or metathesis, one of the olefins having m or p carbon atoms is obtained from bioresources and in particular from isobutene obtained with the method described in applications WO2012052427, WO2017085167 and WO2018206262, for example from polysaccharides (sugars, starches, celluloses, etc).

The co-dimerization step can be conducted in the presence of a catalyst selected from among Brønsted acids in solution, e.g. H2SO4, H3PO4, HF, methanesulfonic acid, triflic acid (CF$_3$SO$_3$H); solid Brønsted acids e.g. organic resins, clays, zeolites, silica supported H3PO4; Lewis, acids e.g. ZnCl2, AlCl3; organometallic compounds e.g. Ni complexes, mixtures of Ni complexes and Al; ionic liquids e.g. [BMIm][N(CF3SO2)2]/HN(CF3SO2)2; clays with lamellar structure such as Montmorillonite; organic resins such as Amberlysts, sulfonic resins; organometallic compounds e.g. [LNiCH$_2$R$^{21}$][AlCl4] where L=PR$^{22}$, R$^{21}$ is a linear or branched alkyl having 9 carbon atoms and R$^{22}$ is a —CH$_2$-R$^{21}$ group.

Preferably the amount of catalyst used for co-dimerization is between 1000 ppm and 10% by weight, more preferably between 1000 ppm and 5% by weight relative to the weight of olefin.

The co-dimerization step is preferably conducted at a temperature of between 30 and 250° C., preferably between 100 and 200° C.

In particularly advantageous manner, the olefins can be obtained from isobutene. Preferably, said isobutene is obtained from bioresources, in particular such as described in application WO2012052427, for example from polysaccharides (sugars, starches, celluloses, etc).

The metathesis step is performed by reacting the two olefins in the presence of a metathesis catalyst, in particular a catalyst selected from among catalysts known to skilled persons for metathesis, in particular ruthenium catalysts, particularly $2^{nd}$ generation Grubbs catalysts e.g. Benzylidene 1,3-bis(2,4,6-trimethylphenyl)-2-imidazolidinylidene dichloro(tricyclohexyl-phosphine)ruthenium or (1,3-dimesitylimidazolidine-2-ylidene)(tricyclohexylphosphine)benzylidene ruthenium dichloride. The amount of catalyst is preferably between 50 ppm and 5% by weight of Ru element, preferably between 200 ppm and 1%, relative to the weight of olefin. The reaction is preferably conducted at a temperature of between 0 and 150° C., for example between 20 and 100° C. The medium is then subjected to a purification step e.g. the reaction medium is dissolved in a solvent e.g. toluene and the mixture obtained is filtered e.g. on neutral alumina.

The present invention also concerns the use of a compound such as defined above meeting aforementioned formula (I) or of the mixture such as defined above as plasticizer, lubricant, surfactant or in a cosmetic composition.

The present invention also concerns the use of a formula (I) compound in which $R^5$=H, to obtain:
 the corresponding acid compound via oxidation; or
 the corresponding alcohol compound via reduction; or a compound of ester type obtained by dismutation (Tishchenko reaction) of two formula (I) compounds.

The oxidation reaction can particularly be oxidation in air or in the presence of d'O$_2$. The reaction can be catalysed by a metal catalyst containing Mn, Co or Cu in particular. The reaction can be conducted at a temperature of between 20 and 200° C., preferably between 50 and 150° C.

The reduction reaction can particularly be a hydrogenation reaction catalysed by a metal catalyst in solution or deposited on a substrate e.g. Raney Ni, Pd/C, Pd/SiO$_2$, Pt/Al$_2$O$_3$. The reaction can be conducted at a temperature of between 20 and 150° C., preferably between 50 and 100° C.

The dismutation reaction can be performed in the presence of a catalyst selected in particular from among CaO, BaO, MgO, preferably CaO. Preferably, the reaction is conducted at a temperature of between 50 and 150° C., preferably between 70 and 120° C. The dismutation reaction can last 5 to 15 h, preferably 7 to 12 h.

The present invention also concerns the products obtained from these oxidation, reduction and dismutation reactions.

The present application is now described with the aid of nonlimiting examples.

EXAMPLES

Example 1: Preparation of Formula (I) Compounds of the Invention

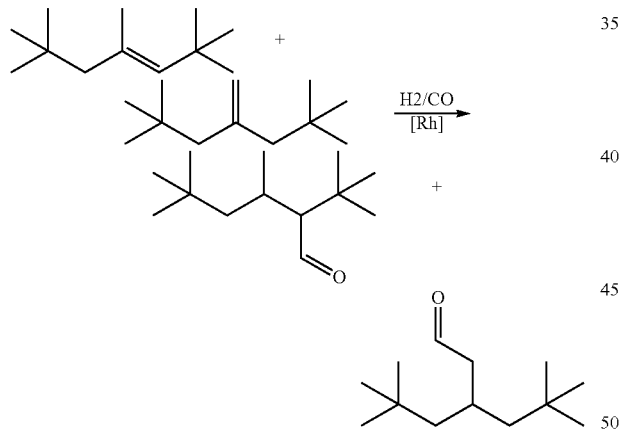

After solubilizing 40 mg (0.156 mmol) of Rh(CO)$_2$(acac) and 466 mg (0.82 mmol) of TPP (triphenyl phosphine) in toluene (150 mL), the addition is made of isododecene (22 mmol). After transferring the solution to a stainless-steel reactor, the system was purged 3 times with argon. The reaction medium was then heated to 80° C. and placed under a pressure of 50 bar Syngas (CO/H2=1:1). The reaction medium was stirred at a speed of 800 rpm. After a heating time of 6 hours, the reactor was cooled to ambient temperature, degassed, and the reaction medium was hydrolysed with 75 mL of water. After extraction with ethyl acetate (3×50 mL), the organic phase was dried over Na$_2$SO$_4$ and concentrated under reduced pressure. The aldehydes were obtained in a mixture in a ratio of 43:56 (Branched/Linear) with a yield of 75%.

Example 2: Oxidation of the Compounds Derived from Example 1

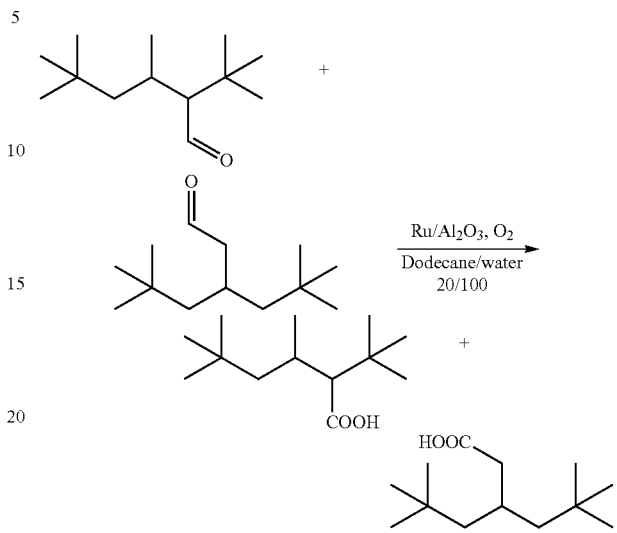

A 300 mL PARR instrument reactor was charged with 15 g of 43:56 aldehyde mixture (B/L=5.5-dimethyl-3-neopentylhexanal) 6 mol % Ru/Al$_2$O$_3$ (5 wt. %), 40 mL of dodecane and 200 mL of water. After purging the system under argon, the reactor was placed under 4 bar oxygen pressure and left under agitation. After heating for 2 hours at 150° C., the reactor was cooled to 25° C. and the reaction medium was filtered. 50 mL of water were added after which the two phases were separated. The aqueous phase was extracted with ethyl acetate 2×40 mL. The combined organic phases were concentrated under reduced pressure to afford the corresponding acids with a good yield of 81%.

Example 3: Reduction of the Compounds Derived from Example 1

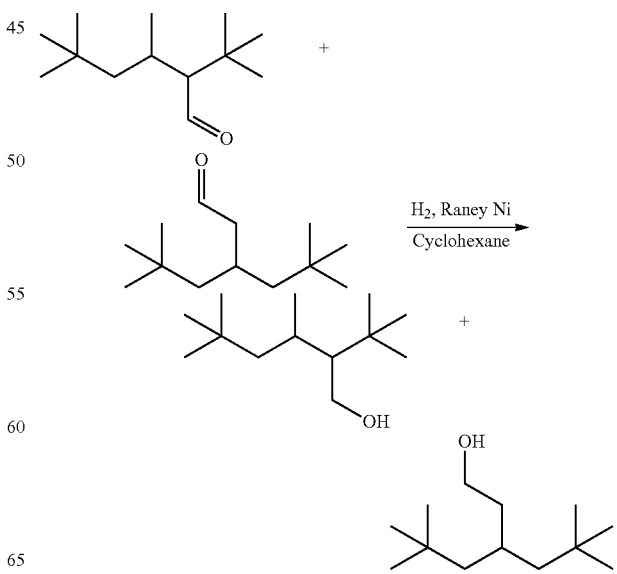

A 300 mL autoclave of PARR instrument type was charged with 10 g of 43:56 aldehyde mixture (B/L=5,5-dimethyl-3-neopentylhexanal) in 120 mL of cyclohexane and 200 mg of Raney Nickel. After purging the system with argon, a pressure of 10 bar hydrogen was set and the autoclave heated to 80° C., mechanical stirring was adjusted to 800 rpm. After a reaction time of 4 hours, the system was cooled to 25° C., the reaction medium was filtered to remove the catalyst and concentrated under reduced pressure to afford a mixture of alcohols with a yield of 92%.

Example 4: Dismutation of the Compounds Derived from Example 1

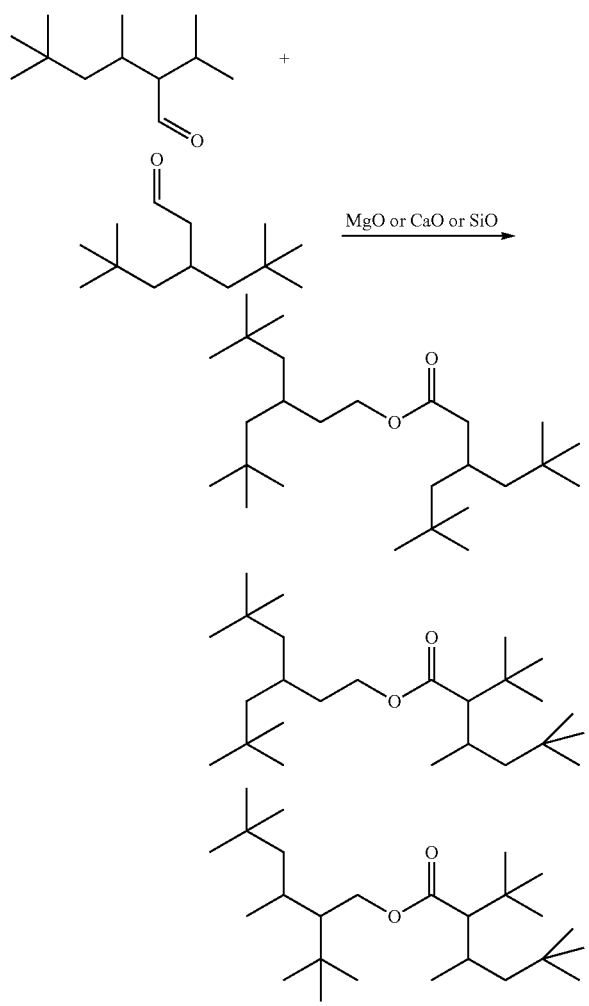

To 100 g of 43:56 aldehyde mixture (B/L=5,5-dimethyl-3-neopentylhexanal) placed in a reactor under perfect agitation, 5 g of calcium oxide were added and the whole heated to 80° C. for 8 hours. After return of the reactor to 25° C., 200 mL of diisopropyl ester or isooctane were added after which the reaction medium was filtered to separate the catalyst. The filtrate was concentrated under reduced pressure leading to the statistical mixture of expected esters with a yield of 76%.

The invention claimed is:

1. A compound of following formula (I):

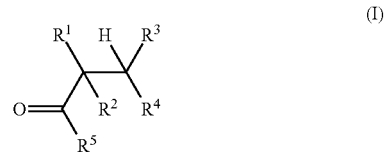

wherein:
$R^1$, $R^2$, $R^3$ and $R^4$ are each independently H or a ($C_1$-$C_{30}$) alkyl group, provided:
the total sum of the number of carbon atoms of $R^1$, $R^2$, $R^3$ and $R^4$ is equal to 6+4x, wherein x is an integer of 1 to 6;
at most two among $R^1$, $R^2$, $R^3$, and $R^4$ are H; and
at least one of groups $R^1$, $R^2$, $R^3$, or $R^4$ comprises or is a tert-butyl group; and
$R^5$ is H, OR, or NR'R", wherein R, R' and R", the same or different, are H or a ($C_1$-$C_{10}$) alkyl group.

2. The compound according to claim 1, wherein $R^5$ is H or OH.

3. The compound according to claim 1, wherein:
x is 1, 4, or 6, or x is 2, 3, 4, 5, or 6; and
$R^5$ is OR or NR'R".

4. A mixture of isomers of branched alkanes functionalised by a C=$OR^5$ function, the mixture comprising a least two compounds of formula (I) according to claim 1.

5. The mixture according to claim 4, wherein all the compounds of formula (I), in addition to the C (O) $R^5$ group, comprise 8+4x carbon atoms, wherein x the same for all the compounds of said mixture.

6. A method of preparing a compound according to claim 1, the method comprising a carbonylation step of at least one isomer of branched olefins, each branched olefin being formed of a hydrocarbon chain having 8+4x carbon atoms.

7. The method according to claim 6, wherein the carbonylation step is performed via organometallic catalysis.

8. The preparation method according to claim 6, wherein the mixture of isomers of branched olefins comprises at least two isomers of branched olefins of following formula (II):

9. A method for preparing a mixture of claim 4, the method comprising a dimerizing a mixture of isomers of branched olefins having 4+2x carbon atoms, with x being an even number.

10. The method according to claim 9, wherein the mixture of isomers of branched olefins is obtained by oligomerization of at least two mixtures of isomers of branched olefins respectively having m and p carbon atoms, wherein m and p, differing, are integers of 4, 8, 12 or 16, and m+p=8+4x.

* * * * *